United States Patent
Bredno et al.

(10) Patent No.: US 8,086,001 B2
(45) Date of Patent: Dec. 27, 2011

(54) UTILIZING PHYSIOLOGICAL MODELS TO CONTROL FUNCTIONAL ACQUISITIONS

(75) Inventors: Joerg Bredno, Aachen (DE); Georg Rose, Duesseldorf (DE); Juergen Weese, Aachen (DE); Alexandra Groth, Aachen (DE); Sabine Mollus, Aachen (DE); Matthias Bertram, Cologne (DE); Jens Wiegert, Aachen (DE); Christoph Neukirchen, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 923 days.

(21) Appl. No.: 12/090,359

(22) PCT Filed: Oct. 6, 2006

(86) PCT No.: PCT/IB2006/053673
§ 371 (c)(1),
(2), (4) Date: Apr. 16, 2008

(87) PCT Pub. No.: WO2007/046025
PCT Pub. Date: Apr. 26, 2007

(65) Prior Publication Data
US 2008/0205723 A1    Aug. 28, 2008

Related U.S. Application Data

(60) Provisional application No. 60/727,437, filed on Oct. 17, 2005.

(51) Int. Cl.
*G06K 9/00* (2006.01)
(52) U.S. Cl. ........................ 382/128; 382/131
(58) Field of Classification Search .................. 382/128, 382/131, 100
See application file for complete search history.

(56) References Cited

U.S. PATENT DOCUMENTS

| | | | |
|---|---|---|---|
| 5,347,570 A | 9/1994 | Haaks | |
| 6,337,992 B1 | 1/2002 | Gelman | |
| 6,535,821 B2 | 3/2003 | Wang et al. | |
| 7,415,093 B2 * | 8/2008 | Tkaczyk et al. | 378/8 |
| 7,522,744 B2 * | 4/2009 | Bai et al. | 382/100 |
| 2003/0108149 A1 | 6/2003 | Tsuyuki | |
| 2003/0161435 A1 | 8/2003 | Ozaki | |
| 2004/0082846 A1 | 4/2004 | Johnson et al. | |
| 2004/0127789 A1 | 7/2004 | Ogawa | |
| 2005/0058331 A1 | 3/2005 | Klotz | |

FOREIGN PATENT DOCUMENTS
EP    0869738 B1    2/2004

OTHER PUBLICATIONS

Bennett, J. R., et al.; A preliminary study on adaptive field-of-view tracking in peripheral digital subtraction angiography; 2003; Journal of X-Ray Science and Technology; 11:149-159.

* cited by examiner

*Primary Examiner* — Louis Arana

(57) ABSTRACT

Adaptively controlling an imaging system (200, 205) includes constructing model feature characteristics (105) of a process over time, determining parameters and commands (110) for controlling the imaging system for each state of the process, performing data acquisition (120) for the process, extracting current features (130) of the process from the acquired data, matching (135) the current features (130) with the model feature characteristics (105) to determine a state of the process (140), and controlling the data acquisition based on the state of the process to produce optimized data.

20 Claims, 4 Drawing Sheets

UTILIZING PHYSIOLOGICAL MODELS TO CONTROL FUNCTIONAL ACQUISITIONS

CROSS REFERENCE TO RELATED APPLICATIONS

This application claims the benefit of U.S. provisional application Ser. No. 60/727,437 filed Oct. 17, 2005, which is incorporated herein by reference.

The embodiments disclosed herein relate to functional imaging for a time-series of image acquisitions where the dynamics of a marker substance or contrast agent are observed.

In addition to conventional static imaging, various dynamic acquisition protocols and analysis algorithms are becoming increasingly available for many different modalities. For example, dynamic acquisition protocols have been developed for modalities like computed tomography (CT), magnetic resonance imaging (MRi), interventional radiology or single photon emission computed tomography (SPECT) and include the analysis of perfusion, blood flow, and tracer kinetics in molecular imaging. This ID also relates to volume imaging of temporarily contrasted structures.

Currently, the most often used method to acquire data for functional imaging is to utilize a fixed protocol, that is, a pre-defined set of technical imaging parameters and the timing of an acquisition. Due to inter-patient variations, such a set might or might not be suitable for a functional acquisition. Each of the possible algorithms for functional analysis of acquired image data usually have different parametric constraints for what is being imaged and to how it is being imaged. The parameters may include, for example, acquisition time, imager geometry, resolution, and tracer or contrast agent dosage. The complexity of image acquisition may increase dramatically when multiple imaging modes, for example, a combination of SPECT and CT, are utilized, because of the dynamic conditions within the patient and the number of controls to adjust.

Mis-adjustment of any of the imaging parameters or the timing of the acquisition commonly results in weak image quality and unreliable functional assessments. As a result, user interaction is generally required to adapt an acquisition to the various dynamic parameters while the acquisition occurs. If a user makes a sub-optimal adjustment, the functional assessment and reconstruction algorithms may provide information of degraded quality. In some instances the degraded quality information may be the only information available.

A significant consideration when imaging is the toxicity or radioactivity of the contrast agents. Administering more contrast agent in order to obtain a proper image, or simply repeating an image acquisition, may be prohibited depending on the amount of contrast agent previously administered. In some cases imaging may have to be suspended. Thus, in some instances, the first time an image is acquired, it should be optimal because further imaging may not be possible. A specific example where the number of acquisitions may be limited is a perfusion study with CT, which is a high x-ray dose modality. Repetition of functional imaging may be undesirable or even prohibited if such acquisitions cause a certain X-ray dose to be exceeded.

It would be advantageous to automatically provide an imager with the proper parametric adjustments during the acquisition process to acquire optimal image data without repeating the acquisition unnecessarily, and while minimizing operator adjustments.

In one embodiment, a method for adaptively controlling an imaging system includes constructing model feature characteristics of a process over time, determining parameters and commands for controlling the imaging system for each state of the process, performing data acquisition for the process, extracting current features of the process from the acquired data, matching the current features with the model feature characteristics to determine a state of the process, and controlling the data acquisition based on the state of the process to produce optimized data.

In another embodiment, an adaptively controlled imaging system includes a controller operable to store model feature characteristics of a process over time, store parameters and commands for controlling the imaging system for each state of the process, perform data acquisition for the process, extract current features of the process from the acquired data, match the current features with the model feature characteristics to determine a state of the process, and control the data acquisition based on the state of the process to produce optimized data.

In still another embodiment, a computer program product includes a computer useable medium having a computer readable program, where the computer readable program when executed on a controller causes the controller to store model feature characteristics of a process over time, store parameters and commands for controlling the imaging system for each state of the process, perform data acquisition for the process, extract current features of the process from the acquired data, match the current features with the model feature characteristics to determine a state of the process, and control the data acquisition based on the state of the process to produce optimized data.

The foregoing aspects and other features of the present invention are explained in the following description, taken in connection with the accompanying drawings, wherein.

Figure 1:
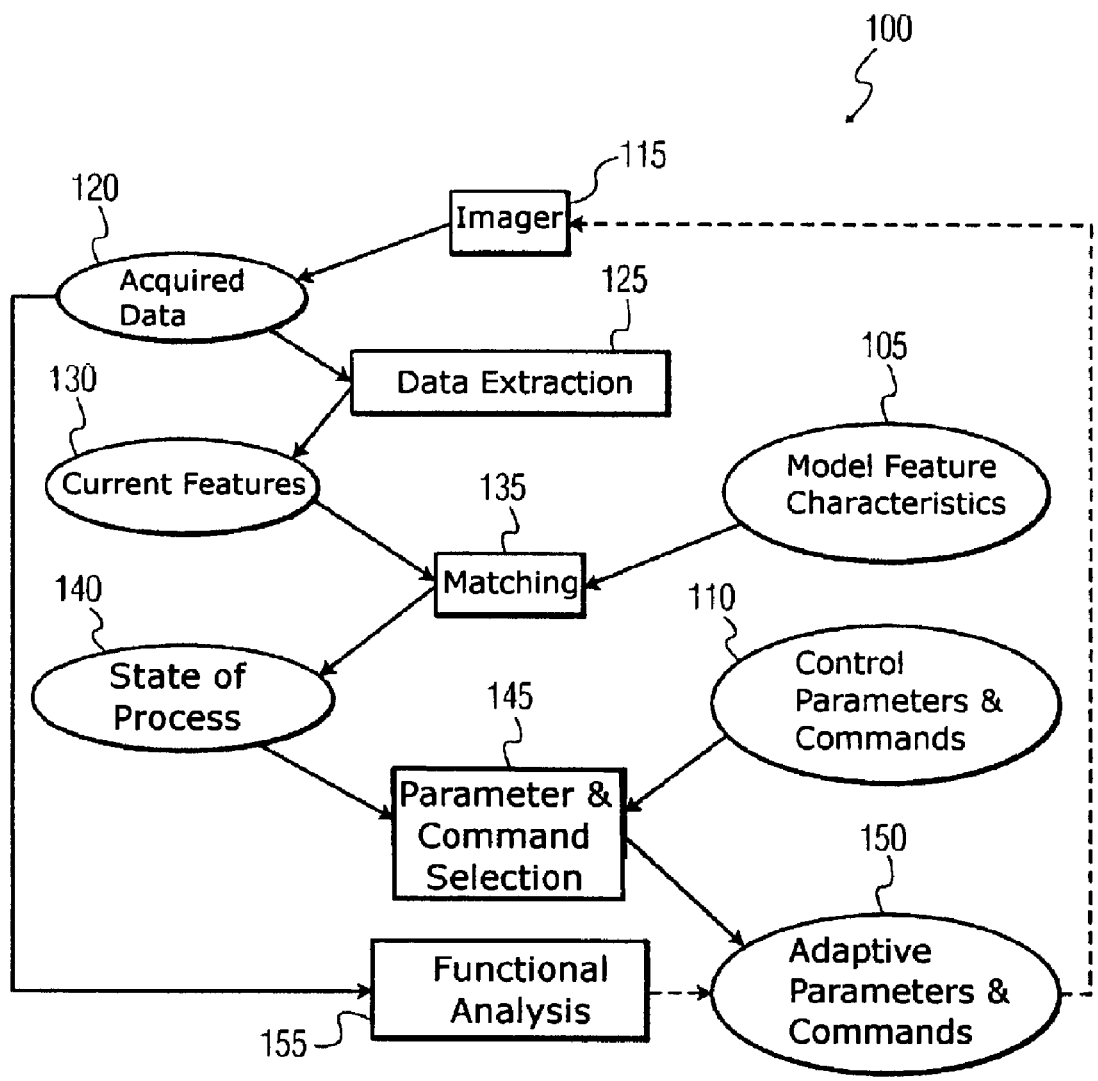
FIG. 1 shows a feedback loop according to the disclosed embodiments for adaptive functional imaging based on comparing model feature information to image data as it is being acquired.

FIG. 1 shows a block diagram of an imaging system 100 suitable for implementing the embodiments disclosed herein. Although the present invention will be described with reference to the embodiment shown in the drawings, it should be understood that the present invention may be embodied in many alternate forms including any combination of hardware and software. In addition, any suitable size, shape or type of materials, elements, computer program elements, computer program code, or computer program modules could be used.

The disclosed embodiments are generally directed to modeling contrast agent dynamics and appearance. It is a feature of the present invention to employ a model of a physiological process. Changes in the appearance of the contrast agent in the image data for the physiological process are modeled on a normalized time scale. By comparing the modeled characteristics with actual characteristics of the physiological process as image data of the process is acquired, the state of the physiological process at the imaging time is determined. Then, imaging and data acquisition parameters may be modified to obtain optimum image data for the particular process state being observed.

FIG. 1 shows a feedback loop 100 for adaptive functional imaging based on comparing model feature information to image data as it is being acquired. The loop includes various processes, referred to as modules, used to implement the features of the disclosed embodiments. While discussed in the context of computer program code, it should be understood that the modules may be implemented in hardware circuitry, computer program code, or any combination of hardware circuitry and computer program code.

As shown in module 105, model feature characteristics of a physiological process over time, such as volumetric vessel flow, area perfusion, pharmaceutical uptake, etc. are constructed. The model feature characteristics may include the change in appearance of the contrast agent on a normalized time scale for the particular process.

The term feature may be used in the context of pattern recognition and may refer to a set of numerical values that describe some expected characteristic of the imaging data. In one example, the model feature characteristics may include expected characteristics of the imaging data, for example, temporal resolution, spatial resolution, gray level contrast, etc. In another example, the model feature characteristics may include representations of various expected states and expected transitions between the states of the physiological process over time.

In module 110, parameters and commands for controlling the imaging system 100 for each state of the particular physiological process are predetermined. Exemplary parameters and commands may include an acquisition start or stop time, imaging rate, spatial or temporal resolution, or any other parameter for controlling an imaging system.

The imager module 115 initiates data acquisition and acquires data 120 about the physiological process as it occurs in a patient. A live feature extraction module 125 analyzes the acquired data to ascertain the current features 130 of the physiological process being observed. The current features 130 are matched with the model feature characteristics 105 of the physiological process in module 135. From this match, the state of the physiological process is determined in module 140. In module 145 parameters and commands from module 110 for controlling the acquisition process are selected based on the state of the physiological process and are conveyed to the imager module 115. The imager module 115 utilizes the imager parameters and commands selected from module 110 to adjust the imaging process in real time to produce optimized acquired data 120.

Thus, the disclosed embodiments provide a live feedback loop 100 where live feature extraction 125, matching 135, parameter and command selection 145, and resulting image process adjustment occur in real time. This produces acquired data 120 that has been optimized for the state of the functional process being observed. As a result, user interaction and any mis-adjustments are reduced or eliminated, and more precise and efficient imaging is obtained.

The optimized acquired data of module 120 is processed by a functional analysis algorithm 155 for the particular physiological process. In one example, the model feature characteristics 105 and the state of the functional process 140 may be related to constraints of the functional analysis algorithm 155, for example, a maximum noise threshold. The current live features 130 may represent the amount of noise actually present in the image data and the model feature characteristics 105 may include a model based on image data noise. If the results of the matching module 135 determine that the state of module 140 represents an image data noise threshold exceeding that required by the functional analysis algorithm 155, image parameters and commands 110 may be selected, also in real time, for the imager 115 in order to reduce the imager data noise.

As an optional part of the disclosed embodiments, the results of the functional analysis algorithm may also be used to modify the imager parameters and commands selected from module 110 by module 145. In one example, an imaging device may have the capability to compute the functional analysis algorithm and then optionally further modify the selected parameters and commands from module 145 to arrive at adaptive parameters and commands 150 for further optimizing the imaging process.

The following exemplary embodiments based on the systems and techniques illustrated above describe the use of the invention and clarify its benefits and advantages. While the following examples are described in the context of CT scanning and interventional x-ray, it should be understood that the present invention is applicable to any suitable scanning technique.

Figure 2A:
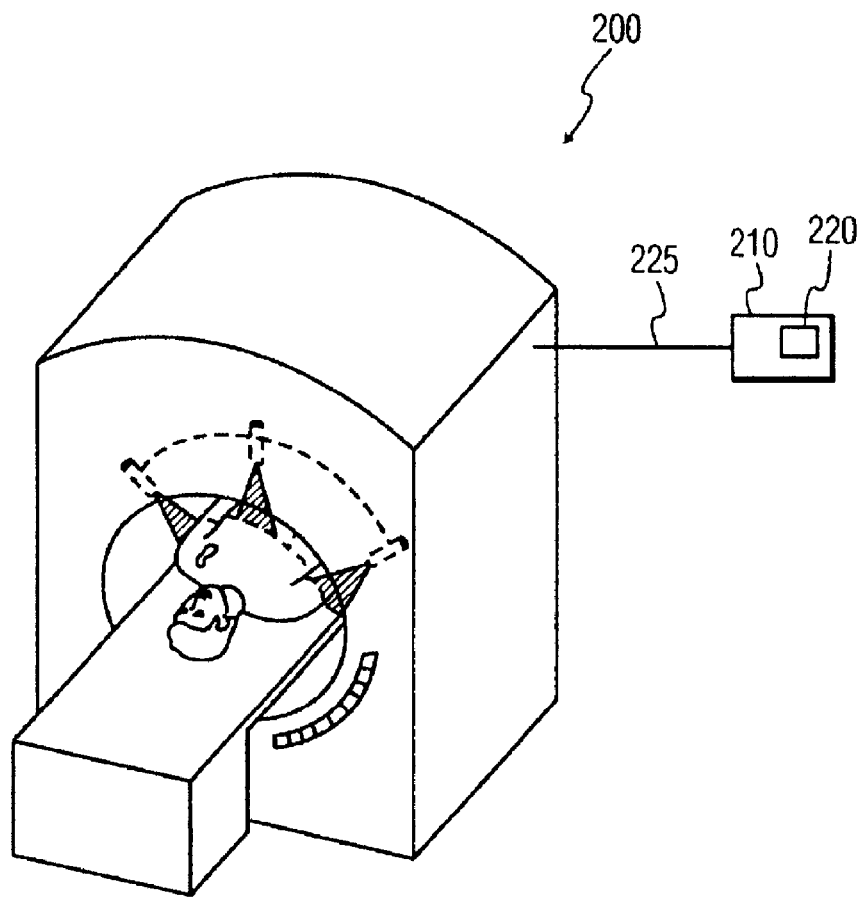
FIGS. 2A and 2B show schematic diagrams of exemplary imaging systems suitable for practicing the disclosed embodiments.
Figure 2B:
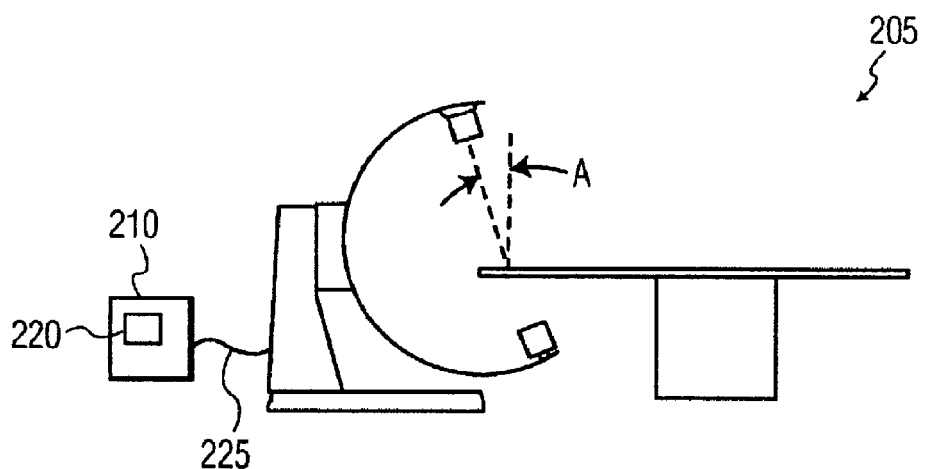

FIG. 2A shows a CT scanner 200. In a preferred embodiment, the scanner is a multi-slice imager and provides axial scanning. FIG. 2B shows an interventional x-ray imager, preferably capable of volume imaging with a rotational acquisition. Each scanner may be connected to a controller 210 through a link 225 capable of real time data communication The controller may have a program storage 220 including a computer usable medium, for example, a diskette, a computer hard drive, a compact disk, a digital versatile disk, an optical disk, a chip, a semiconductor, or any other device capable of storing programs in the form of computer readable code. The program storage 220 is capable of storing and utilizing the model feature characteristics 105 and imager parameters and commands 110. The computer readable program code, when executed by the controller 130, causes the controller 130 to perform the actions described herein and to implement the modules and procedures described herein.

As mentioned above, various imaging techniques may utilize a contrast agent administered to the patient. For perfusion studies or contrast intake studies, a bolus injection of the contrast agent may be administered, where a large quantity of contrast agent is injected.

For an exemplary CT perfusion study according to the prior art, multi-slice imaging may be used to repeatedly acquire a small set of slices over a fixed time span to image the uptake of the contrast agent in the feeding arteries, the early uptake of contrast agent in healthy tissue, and the delayed and reduced contrast agent uptake in the penumbra of infarction regions. The uptake of the contrast agent in the feeding arteries is used to determine the input function to the perfused areas. The system begins to acquire slices at a fixed time after contrast agent injection, e.g. approximately 5 seconds. The slices are acquired with maximal time resolution for a fixed amount of time, for example, approximately 40 seconds.

The prior art protocol may be replaced with the procedure disclosed herein as shown in FIG. 1, including comparing modeled characteristics with actual characteristics of the perfusion study as image data is acquired, determining the state of the physiological process or the imaging process, and adjusting imager parameters and commands in real time to obtain optimum imaging data.

Figure 3:
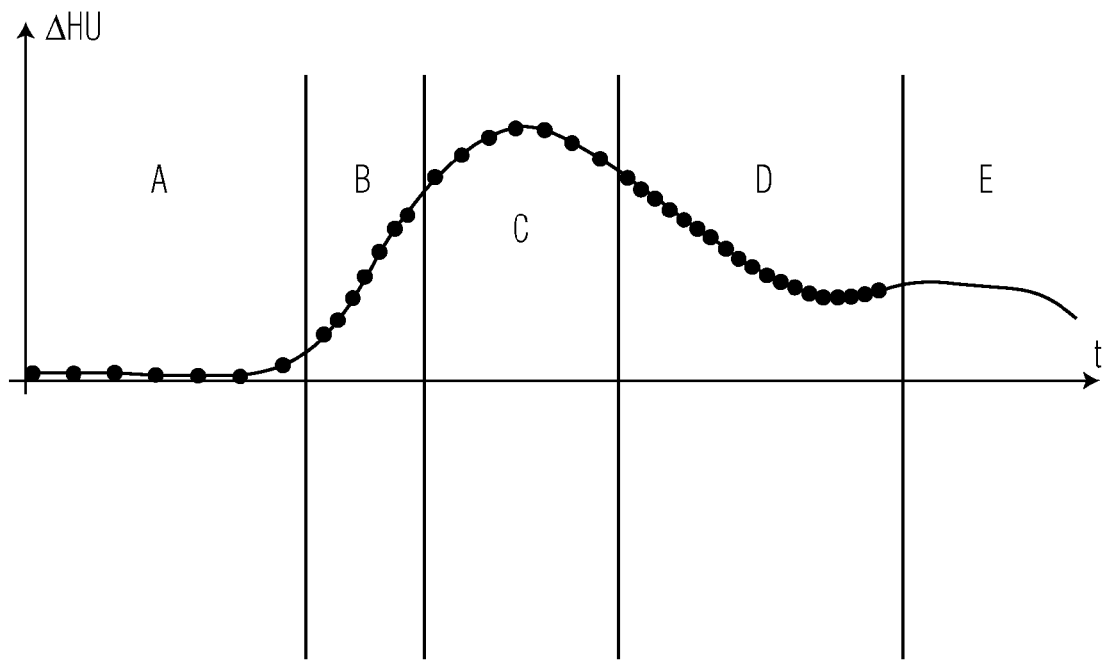
FIG. 3 shows exemplary model feature characteristics for a perfusion study.

FIG. 3 shows an example of model feature characteristics 105 (FIG. 1) for a perfusion study. This particular set of characteristics is expressed in terms of total additional attenuation in Hounsfield units over time. Imager parameters and commands 110 are determined for each state A-E of the model feature characteristics.

For a perfusion study involving penumbra assessment or tissue viability assessment, image data with little contrast agent attenuation is not generally of interest, but the arrival of the contrast agent bolus is. Once the bolus arrives, a high acquisition rate may be required for a short period of time to determine an input function of the perfusion analysis. Unaffected tissue provides a good match with the model and may require less frames. In a candidate time span of delayed infarction penumbra attenuation, a higher frame rate may be required to accurately capture the pathology.

Figure 4:
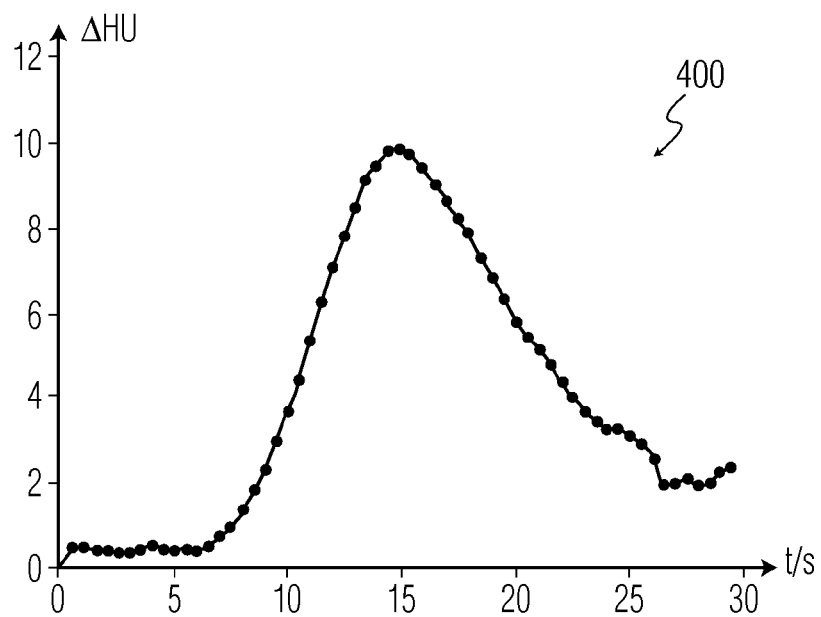
FIG. 4 shows current features extracted from imager data in real time.

FIG. 4 represents the current features 130 resulting from the live feature extraction 125.

Referring again to FIG. 3, in state A the model shows an essentially flat, low attenuation indicating the contrast agent has not yet arrived in the area being observed. The imager parameters for this state would typically include a low acquisition speed or low-dose imaging. An increase in the slope of the attenuation curve indicates that state B has been reached where the contrast agent is visible and a relatively high image acquisition rate may be required to accurately capture the fast uptake in the vessels. In state C, the slope of the attenuation approaching a peak and then becoming negative indicates venous outflow and that the healthy tissue has been perfused, thus dictating a moderate acquisition speed. State D during the continuing decrease in slope is the time for possible penumbra attenuation and requires a maximum image acquisition rate to capture the pathology. In state E, the contrast agent arrives again after traversing the vascular system a second time and the image acquisition ends.

The characteristics and corresponding imager parameters and commands for each state shown in the model of FIG. 3 may be utilized in module 110 of the live feedback loop of FIG. 1. The feedback loop 100 of FIG. 1 then operates to obtain image data that has been optimized in real time for processing by the functional analysis algorithm 155.

In another embodiment, a combined three dimensional flow and perfusion acquisition may be achieved by using the live feedback loop and modules of FIG. 1. While the following example is described using an interventional C-arm imager as shown in FIG. 2B, it should be understood that any suitable scanning system may be used.

In the combined acquisition, one contrast agent dose may be used to identify both the flow in feeding arteries and the transit of the contrast agent through a perfusion area. The combined acquisition may include a relatively fast rotational acquisition with a relatively high acquisition rate for flow quantification, and a slow rotational acquisition, preferably in a reverse direction, for perfusion imaging. The rotational acquisitions of the flow and perfusion phenomena generally require precise timing which the embodiments herein are capable of providing.

For such a combined functional acquisition, different sets of acquired data 120 may be used with one or more functional analysis algorithms 155. Features utilized in the model 105 may include the amount of contrast agent in the image, and the results of vessel filtering techniques.

Figure 5:
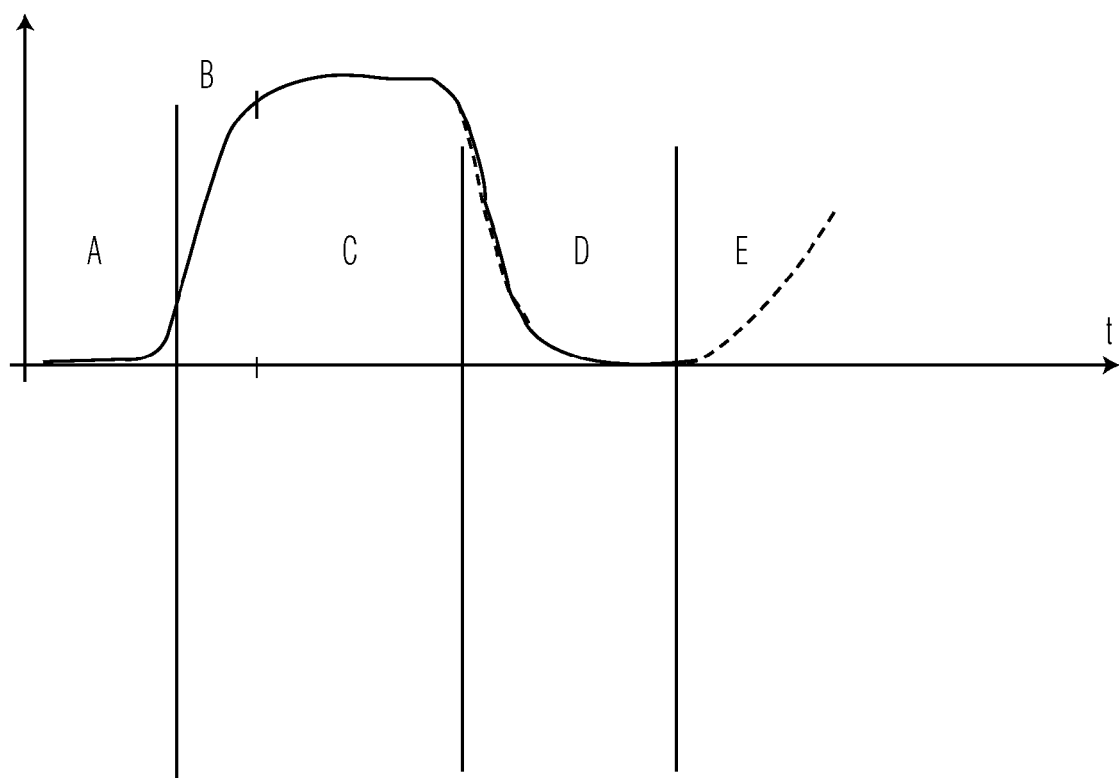
FIG. 5 shows exemplary model feature characteristics for a combined functional acquisition of a vascular system.

FIG. 5 shows an example of model feature characteristics 105 for such a combined functional acquisition. The characteristics are defined in terms of vessel filter results over time as they relate to the presence of the contrast agent in visible vessels, which is used to adapt rotational speed of the imager, scan direction, and acquisition rate for each state of the combined flow and perfusion process. Imager parameters and commands for the rotational speed, scan direction, and acquisition rate may be determined for each state of the combined process and used in module 110.

Figure 6:
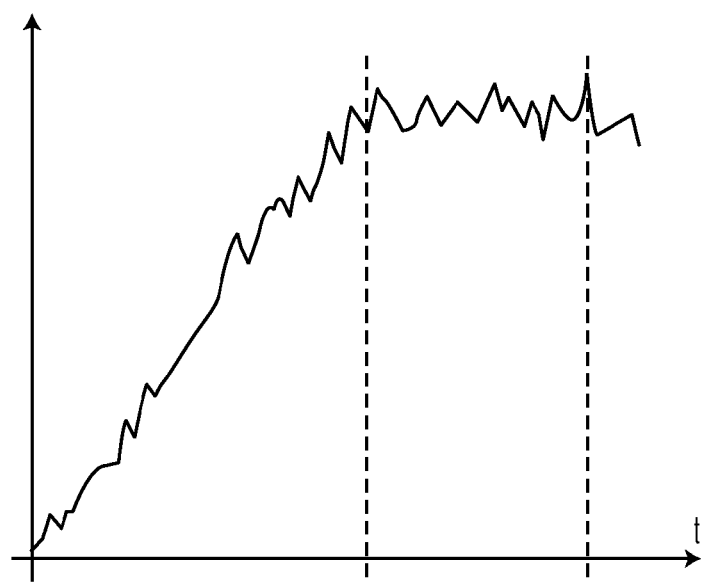
FIG. 6 shows current features extracted from imager data in real time for the above combined acquisition.

FIG. 6 shows the current features 130 that result from the operation of the live feature extraction module 125 also in terms of vessel filter results over time.

Turning to FIG. 5, in state A, image acquisition begins stationary at start position and with a low X-ray dose to detect the arrival of the contrast agent in vessels that precede the vessel or vessel tree of interest. As the value of the filter results begins to increase, indicating an inflow state, flow acquisition may begin in state B with a high rotation speed and high image acquisition rate.

In state C, all vessel structures that are visible for the vessel filters in use have appeared and the perfusion analysis may begin. At this time, contrast agent injection may be discontinued. During this state the imager continues to rotate, in one embodiment, to the end of its travel. It should be understood that state B and C may overlap, that is, the flow and perfusion analysis may overlap. It is also important to note that the flow analysis occurs relatively early and quickly in the combined functional acquisition with the imager rotating as fast as possible so that the process may be acquired from all different directions, while the perfusion analysis occurs in the later stages of the analysis and requires a longer period of time and a slower rotation speed.

In state D, the value of the vessel filter results begins to drop. The imager may be operated at a slower rotational speed and acquisition rate, and in one embodiment may be rotated in a reverse direction, from the end of its travel to its starting point. In another embodiment, if time permits, the imager may be returned to its original staring point for this portion of the analysis. The rotational speed for the perfusion analysis occurring during this state may be optimized for the expected transit time of the bolus through the tissue of interest. In state E, the contrast agent arrives again after traversing the vascular system a second time and image acquisition ends.

The characteristics and corresponding imager parameters and commands for each state shown in the model of FIG. 5 may be utilized in module 110 of the live feedback loop of FIG. 1. The feedback loop 100 of FIG. 1 then operates to obtain image data that has been optimized in real time for processing by the functional analysis algorithm 155.

As mentioned above, there may be more than one functional analysis algorithm 155. In that case, optimized acquired data may be provided to different functional analysis algorithms at different times. For example, when image acquisition for the flow analysis is complete, the acquired data for the flow analysis may be provided to a functional analysis algorithm for flow analysis while data acquisition continues for the perfusion analysis. The live feedback loop may also have the additional advantage of being able to automatically distribute the acquired data 120 to the different functional analysis algorithms 155 without user interaction.

Thus, the embodiments disclosed herein offer multiple advantages including higher image quality by providing subsequent reconstruction and analysis algorithms with tailored acquisitions, reduced user interaction and improved ease-of-use by automated algorithm-adaptive determination of imager parameters. The disclosed embodiments also provide the capability to perform different types of acquisitions using different time scales (e.g. flow and perfusion), and avoidance of repeated acquisitions by optimizing data acquisition in real time.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A method for adaptively controlling an imaging system comprising:
constructing model feature characteristics of a process over time;
determining parameters and commands for controlling the imaging system for each state of the process;
performing data acquisition for the process;
extracting current features of the process from the acquired data;
matching the current features with the model feature characteristics to determine a state of the process; and
controlling the data acquisition based on the state of the process to produce optimized data.

2. The method of claim 1 wherein performing data acquisition for the process, extracting current features of the process from the acquired data, matching the current features with the model feature characteristics to determine a state of the process, and controlling the data acquisition based on the state of the process are performed in real time.

3. The method of claim 1 wherein controlling the data acquisition includes specifying at least one of an acquisition start time, an acquisition stop time, an imaging rate, a spatial resolution, and a temporal resolution.

4. A non-transitory computer readable medium containing a computer program product having instructions that when executed on one or more processors causes the one or more processors to perform the method of claim 1.

5. The method of claim 1, wherein the model feature characteristics include a volumetric vessel flow, an area perfusion, as pharmaceutical uptake, a change in appearance of a contrast agent.

6. A method for adaptively controlling an imaging system comprising:
constructing model feature characteristics of a process over time;
determining parameters and commands for controlling the imaging system for each state of the process;
performing data acquisition for the process;
extracting current features of the process from the acquired data;
matching the current features with the model feature characteristics to determine a state of the process;
controlling the data acquisition based on the state of the process to produce optimized data and
performing a functional analysis of the optimized data.

7. The method of claim 6, further comprising further controlling the data acquisition using results of the functional analysis.

8. The method of claim 6, wherein performing data acquisition for the process, extracting current features of the process from the acquired data, matching the current features with the model feature characteristics to determine a state of the process, and controlling the data acquisition based on the state of the process are performed in real time.

9. The method of claim 6, wherein controlling the data acquisition includes specifying at least one of an acquisition start time, an acquisition stop time, an imaging rate, a spatial resolution, and a temporal resolution.

10. A non-transitory computer readable medium containing instructions for controlling a processor to perform the method of claim 6.

11. A system having a controller operable to perform the method of claim 6.

12. The method of claim 6, wherein the model feature characteristics include at least one of a volumetric vessel flow, an area perfusion, a pharmaceutical uptake.

13. The method of claim 6, wherein the model feature characteristics include a change in appearance of a contrast agent.

14. The method of claim 6, wherein the optimized data is provided to different functional analysis algorithms at different times.

15. An adaptively controlled imaging system comprising:
a controller operable to:
store model feature characteristics of a process over time;
store parameters and commands for controlling the imaging system for each state of the process;
perform data acquisition for the process;
extract current features of the process from the acquired data;
match the current features with the model feature characteristics to determine a state of the process; and
control the data acquisition based on the state of the process to produce optimized data.

16. The system of claim 15 wherein the controller performs data acquisition for the process, extracts current features of the process from the acquired data, matches the current features with the model feature characteristics to determine a state of the process, and controls the data acquisition based on the state of the process in real time.

17. The system of claim 15 wherein the controller controls the data acquisition based on the state of the process by specifying at least one of an acquisition start time, an acquisition stop time, an imaging rate, a spatial resolution, and a temporal resolution.

18. The system of claim 15, wherein the controller is operable to perform a functional analysis of the optimized data.

19. The system of claim 18, wherein the controller is operable to further control the data acquisition using results of the functional analysis.

20. The system of claim 15, wherein the model feature characteristics include a volumetric vessel flow, an area perfusion, as pharmaceutical uptake, a change in appearance of a contrast agent.

* * * * *